US010448920B2

(12) United States Patent
Patel et al.

(10) Patent No.: US 10,448,920 B2
(45) Date of Patent: Oct. 22, 2019

(54) COUGH DETECTING METHODS AND DEVICES FOR DETECTING COUGHS

(75) Inventors: Shwetak N. Patel, Seattle, WA (US); Eric Cooper Larson, Garland, TX (US); Tien-Jui Lee, Seattle, WA (US); Shih-Yen Liu, Hong Kong (HK)

(73) Assignee: University of Washington, Seattle, WA (US)

( * ) Notice: Subject to any disclaimer, the term of this patent is extended or adjusted under 35 U.S.C. 154(b) by 730 days.

(21) Appl. No.: 14/343,374

(22) PCT Filed: Sep. 14, 2012

(86) PCT No.: PCT/US2012/055614
§ 371 (c)(1),
(2), (4) Date: Jun. 23, 2014

(87) PCT Pub. No.: WO2013/040485
PCT Pub. Date: Mar. 21, 2013

(65) Prior Publication Data
US 2014/0336537 A1 Nov. 13, 2014

Related U.S. Application Data

(60) Provisional application No. 61/535,174, filed on Sep. 15, 2011.

(51) Int. Cl.
*A61B 7/04* (2006.01)
*A61B 7/00* (2006.01)
(Continued)

(52) U.S. Cl.
CPC .............. *A61B 7/04* (2013.01); *A61B 5/0823* (2013.01); *A61B 7/003* (2013.01); *G10L 25/66* (2013.01)

(58) Field of Classification Search
CPC .......... A61B 7/04; A61B 5/0823; G10L 25/66
See application file for complete search history.

(56) References Cited

U.S. PATENT DOCUMENTS 6,954,721 B2 * 10/2005 Webber ................... G06F 17/15
375/343
7,207,948 B2 * 4/2007 Coyle .................. A61B 5/0476
600/529

(Continued)

FOREIGN PATENT DOCUMENTS

WO 2013/040485 A2 3/2013
WO WO 2014079483 A1 * 5/2014 ......... G10L 21/0232

OTHER PUBLICATIONS

Neal, Lawrence, et al. "Time-frequency segmentation of bird song in noisy acoustic environments." Acoustics, Speech and Signal Processing (ICASSP), 2011 IEEE International Conference on. IEEE, 2011.*

(Continued)

*Primary Examiner* — Daniel L Cerioni
*Assistant Examiner* — Yasmeen S Warsi
(74) *Attorney, Agent, or Firm* — Dorsey & Whitney LLP

(57) ABSTRACT

Examples of the present invention utilize principal component analysis (PCA) to detect cough sounds in an audio stream. Comparison of all or portions of the audio stream with a cough model may be conducted. The cough model may include a number of basis vectors may be based on initial portions of known coughs. The initial portions may be non-user specific, and accordingly the cough model may be used to detect coughs across individuals. Moreover, examples of the present invention may reconstruct the cough sounds from stored features such that the cough sounds are reconstructed but the reconstruction techniques used may be (Continued)

insufficient to reconstruct speech sounds that may also have been recorded, which may increase user privacy.

20 Claims, 2 Drawing Sheets

(51) Int. Cl.
    *A61B 5/08*           (2006.01)
    *G10L 25/66*         (2013.01)

(56) References Cited

U.S. PATENT DOCUMENTS

| | | |
|---|---|---|
| 2008/0306367 A1 | 12/2008 | Koehler et al. |
| 2009/0312660 A1 | 12/2009 | Guarino et al. |
| 2011/0075851 A1 | 3/2011 | Leboeuf et al. |
| 2011/0125044 A1 | 5/2011 | Rhee et al. |

OTHER PUBLICATIONS

International Search Report and Written Opinion for International Application No. PCT/US12/55614, dated Mar. 4, 2013.
Abaza, et al., "Classification of voluntary cough sound and airflow patterns for detecting abnormal pulmonary function", Cough, vol. 5; Issue 1, ISSN 17459974. Nov. 20, 2009, 1-12.
Barry, et al., "The automatic recognition and counting cough", Cough, vol. 2; Issue 1, ISSN 17459974, Sep. 28, 2006, 1-9.
AsthmaMD (retrieved Apr. 2015) http://www.asthmamd.org, 1 pg.
Barry, et al., "The automatic recognition and counting of cough", Cough, 2:8, Sep. 2006, 9 pgs.
Bickerman, et al., "The effect of a new bronchodilator aerosol on the airflow dynamics of the maximal voluntary cough of patients with bronchial asthma and pulmonary emphysema", Journal of Chronic Diseases, 8(5), Nov. 1958, pp. 629-636.
Boersma, et al., "Praat: doing phonetic by computer", retrieved Apr. 2015, http://www.praat.org, 2 pgs.
Breiman, "Random Forests", Machine Learning, 45(1), Oct. 2001, pp. 5-32.
Chang, et al., "Relationship between cough, cough receptor sensitivity and asthma in children", Pulmonary Pharmacology & Therapeutics, 15(3), May 2002, pp. 287-291.
Cherry, et al., "National Ambulatory Medical Care Survey: 2006 Summary", National Health Statistics Reports, (3), Aug. 2008, pp. 1-40.
Chiu, et al., "Playful Bottle: a Mobile Social Persuasion System to Motivate Healthy Water Intake", Proceedings of the 11th Int'l Conference on Ubiquitous Computing (UbiComp '09), Sep./Oct. 2009, pp. 185-194.
Chung, et al., "Prevalence, pathogenesis, and causes of chronic cough", The Lancet, 371 (9621), Apr. 2008, pp. 1364-1374.
Consolvo, et al., "Activity Sensing in the Wild: A Field Trial of UbiFit Garden", Proceedings of the SIGCHI Conference on Human Factors in Computing Systems (CHI '08), Apr. 2008, pp. 1797-1806.
Decalmer, et al., "Chronic cough: how do cough reflex sensitivity and subjective assessments correlate with objective cough counts during ambulatory monitoring?", Thorax, 62(4), Apr. 2007, pp. 329-334.
Gibson, et al., "CICADA: Cough in Children and Adults: Diagnosis and Assessment. Australian Cough Guidelines summary statement", Medical Journal of Australia, 192(5), Mar. 2010, pp. 265-271.
Gross, et al., "Mobile nocturnal long-term monitoring of wheezing and cough", Biomedizinische Technik (Biomedical Engineering), 52(1), Feb. 2007, pp. 73-76.
Hoglund, et al., "A method of determining the cough threshold with some preliminary experiments on the effect of codeine", Acta Physiologica Scandinavica, 21(2-3), Apr. 1950, pp. 168-173.

Irwin, et al., "Diagnosisand Management of Cough Executive Summary: ACCP Evidence-Based Clinical Practice Guidelines", Chest, 129(1 Suppl.): 1S-23S, Jan. 2006, 33 pgs.
Kerem, et al., "Ambulatory quantitative waking and sleeping cough assessment in patients with cystic fibrosis", Journal of Cystic Fibrosis, 10(3), May 2011, pp. 193-200.
Kerem, et al., "Effectiveness of PTC124 treatment of systic fibrosis caused by nonsense mutations: a prospective phase II trial", Lancet, 372(9640), Aug. 2008, pp. 719-727.
Korpas, et al., "Analysis of the cough sound: an overview", Pulmonary Pharmacology, 9(5-6), Oct.-Dec. 1996, pp. 261-268.
Kraman, et al., "Comparison of lung sound transducers using a bioacoustic transducer testing system", Journal of Applied Physiology, 101(2), Aug. 2006, pp. 469-476.
Larson, et al., "Accurate and Privacy Preserving Cough Sensing using a Low-Cost Microphone", Proceedings of the 13th Int'l Conference on Ubiquitous Computing (UbiComp '11), Sep. 2011, pp. 375-384.
Miravitlles, et al., "Pharmacoeconomic Evaluation of Acute Exacerbations of Chronic Bronchitits and COPD", Chest, 121(5), May 2002, pp. 1449-1455.
Morice, et al., "ERS guidelines on the assessment of cough", European Respiratory Journal, 29(6), Jun. 2007, pp. 1256-1276.
Newcombe, et al., "Validation of a parent-proxy quality of life questionnaire for pediatric chronic cough (PC-QOL)", Thorax, 65(9), Sep. 2010, pp. 819-823.
Pathak, "Privacy Preserving Techniques for Speech Processing", PhD Thesis, Carnegie Mellon University, Dec. 2010, 54 pgs.
Pearson, "On Lines and Planes of Closest Fit to Systems of Points in Space", Philosophical Magazine Series 6, 2(11), epub. Jun. 2010, pp. 559-572.
Piirila, et al., "Objective assessment of cough", European Respiratory Journal, 8(11), Nov. 1995, pp. 1949-1956.
Raj, et al., "Clinical assessment of chronic cough severity", Pulmonary Pharmacology & Therapeutics, 20(4), Aug. 2007, pp. 334-337.
Sanders, et al., "Return of FEV1 after Pulmonary Exacerbation in Children with Cystic Fibrosis", Pediatric Pulmonology, 45(2), Feb. 2010, pp. 127-134.
Schappert, et al., "Ambulatory Care Visits to Physician Offices, Hospital Outpatient Departments, and Emergency Departments: United States 2001-02", Vital and Health Statistics, Series 13, No. 159, Feb. 2006, 73 pgs.
Seemungal, et al., "Time Course and Recovery of Exacerbations in Patients with Chronic Obstructive Pulmonary Disease", American Journal of Respiratory and Critical Care Medicine, 161(5), May 2000, pp. 1608-1613.
Smith, et al., "New Devolopments in the Objective Assessment of Cough", Lung, 186(1), Feb. 2008, pp. 48-54.
Spencer, et al., "Time course of recovery of health status following an infective exacerbation of chronic bronchitis", Thorax, 58(7), Jul. 2003, pp. 589-593.
Wilcoxon, "Individual Comparisons by Ranking Methods", Biometrics Bulletin, 1(6), Dec. 1945, 5 pgs.
Witten, et al., "Data Mining: Practical Machine Learning Tools and Techniques, 2nd Edition, Morgan Kaufmann Publishers, San Francisco", Pub. 2005, 558 pgs.
World Heath Organization, "Cough and Cold Remedies for the Treatment of Acute Respiratory Infections in Young Children", http://www.who.int/maternal_child_adolescent/documents/fch_cah_01_02/en/, Retrieved Mar. 2015, 43 pgs.
Wyatt, et al., "Conversation Detection and speaker Segmentation in Privacy-Sensitive Situated Speech Data", Proceedings of the 8th Annual Conference of the Int'l Speech Communication Association, Aug. 2007, 4 pgs.
Birring, et al.: "The Leicester Cough Monitor: preliminary validation of an automated cough detection system in chronic cough", European Respiratory Journal, vol. 31, No. 5, Jan. 2008, 1013-1018.
Chen, et al., "Audio Privacy: Reduced Speech Intelligibility while Preserving Environmental Sounds", Proceedings of the 16th ACM International Conference on Multimedia, Oct. 2008, 733-736.

(56) References Cited

OTHER PUBLICATIONS

Coyle, et al., "Evaluation of an ambulatory system for the quantification of cough frequency in patients with chronic obstructive pulmonary disease", Cough Journal, Aug. 4, 2005, 1-7.

Hotelling, Harold, "Analysis of a Complex of Statistical Variables Into Principal Components", Journal of Educational Psychology, 1933, 417-441.

Khan, et al., "Classification and diagnostic prediction of cancers using gene expression profiling and artificial neutral networks", Nature Medicine; www.medicine.nature.com, vol. 7, No. 6, Jun. 2001, 673-679.

Matos, Sergio et al., "Detection of Cough Signals in Continuous Audio Recordings Using Hidden Markov Models", IEEE Transactions on Biomedical Engineering, vol. 53, No. 6, Jun. 2006, 1078-1083.

McGuinness, et al., "The Leicester Cough Monitor: a semi-automated, semi-validated cough detection system", European Respiratory Journal, vol. 32, No. 2, Jan. 2009, 529.230.

McGuinness, Kelsall, "Automated Cough Detection, a Novel Approach", Am J Resp Crit Care Med, 2007.

Pinkowski, Ben "Principal Component Analyses of Speech Spectrogram Images", Pattern Recognition, vol. 30, No. 5, 1997, 777-787.

Turk, et al., "Face Recognition Using Eigenfaces", IEEE Conference on Computer Vision and Pattern Recognition, Jun. 1991, 586-591.

\* cited by examiner

COUGH DETECTING METHODS AND DEVICES FOR DETECTING COUGHS

CROSS-REFERENCE TO RELATED APPLICATION(S)

This application claims the benefit of the earlier filing date of U.S. Provisional Application 61/535,174, filed Sep. 15, 2011, entitled "Medical sensing from a mobile phone microphone," which application is hereby incorporated by reference in its entirety for any purpose.

TECHNICAL FIELD

Examples described herein relate generally to cough detection and examples are described of audio-based cough detection devices and methods.

BACKGROUND

Coughing is a common symptom which may result in significant health care costs, medical consultations, and medication use. Proper diagnosis, monitoring, and management of coughs for an individual or population individuals may be of importance.

One conventional method for monitoring coughs includes self-reporting by the individual, which tends to be highly inaccurate. Other known methods for monitoring coughs include automatic cough detection systems which measure thoracic pressure changes in order to determine whether a cough has occurred and thus monitor the frequency of coughs. However, such thoracic pressure based systems tend to be very expensive and cumbersome, as the individual may be required to wear specialized pressure measuring equipment or clothing.

More recent developments in cough detection include certain advances in audio-based cough detection. However, known methods for audio-based detection of coughs generally expose private information about the individual to the person or entity monitoring or classifying the cough. For example, one currently known audio-based detection system is the Leicester Cough Monitor (LCM) system which uses a lapel microphone with a portable audio recorder. However, the LCM system is not only semi-autonomous as it requires human annotators to listen and discard false positives, but is also a poor performer when it comes to preserving audio privacy. The LCM methodology reveals not only speech but also inflections and prosody in the recorded audio. As such, conventional audio-based detection systems may be poorly adapted to offer both accuracy and privacy protection features. The examples described herein may address some or all of the shortcomings in the art, as well as provide additional benefits.

SUMMARY

The summary is provided here by way of example and is not intended to limit the scope of any of the described examples or claims.

Examples of the present invention include tangible computer readable media encoded with instructions. The instructions, when executed, may cause a computing system to receive an audio signal from a microphone, convert at least a portion of the audio into a frequency-based matrix representation, transform the frequency-based matrix into a lesser dimensional matrix using projections from a set of basis vectors in a cough model, and classify at least a portion of the audio signal as corresponding to a cough based, at least in part, on the lesser dimensional matrix.

The instructions, when executed, may in some examples further cause the computing system to classify multiple portions of the audio signal as respective multiple coughs and the multiple coughs as a cough epoch, at least in part, on the lesser dimensional matrix.

In some examples, the frequency-based matrix representation of the at least a portion of the audio signal is an audio spectrogram.

In some examples, the basis vectors of the cough model include eigenvectors of a covariance matrix of frequency-based matrix representations of audio signals corresponding to known cough sounds. In some examples, the basis vectors of the cough model include magnitude spectrograms of audio signals corresponding to known cough sounds. In some examples, the basis vectors of the cough model include complex spectrograms of audio signals corresponding to known cough sounds.

In some examples, the instructions which, when executed, cause the computing system to classify at least a portion of the audio signal as corresponding to a cough include instructions for calculating a score for one or more of the basis vectors in the cough model. In some examples, the instructions that, when executed, cause the computing system to classify at least a portion of the audio signal as corresponding to a cough include instructions for comparing the calculated scores for the one or more basis vectors to threshold values and discarding portions of the transformed audio signal having calculated scores below a predetermined threshold value. In some examples, the instructions that, when executed, cause the computing system to classify at least a portion of the audio signal as corresponding to a cough include instructions for implementing a random forest classifier based on a comparison of the lesser dimensional matrix representation of the at least a portion of the audio signal with the basis vector representation of the cough model.

The cough model may be a non-user specific cough model. The cough model may be stored in a memory accessible to the computing system. The computing system may include a mobile phone.

In some examples, at least in part to preserve privacy, the basis vectors and lesser dimensional matrix may be used to reconstruct the at least a portion of the audio signal corresponding to the cough, but may not effectively reconstruct speech sounds.

In some examples, computer readable media may be further encoded with instructions that, when executed, cause the computing system to reconstruct the at least a portion of the audio signal using multiplication of the basis vectors with the lesser dimensional matrix.

In some examples, the instructions that cause the computing system to reconstruct the at least a portion of the audio signal include instructions for implementing an iterative reconstruction approach including minimizing differences between the frequency based representation of the at least a portion of the audio signal, and a reconstructed frequency-based representation.

In some examples, the instructions, when executed, may also cause the computing system to store a duration of the cough, frequency of multiple coughs in the audio signal, number of coughs in the audio signal, cough epochs in the audio signal, or combinations thereof.

Examples of the present invention include devices. An example device may include a microphone, at least one processor, and a memory encoded with computer readable instructions that, when executed, cause the at least one processor to receive an audio signal from a microphone, convert at least a portion of the audio into a frequency-based matrix representation, transform the frequency-based matrix into a lesser dimensional matrix using projections from a set of basis vectors in a cough model, and classify a portion of the audio signal as corresponding to a cough based, at least in part, on the lesser dimensional matrix.

The devices may be implemented using a mobile phone. In some examples, the memory may be further configured to store the cough model.

Example devices may further include a network interface. The instructions, when executed, may further cause the at least one processor to transmit the lesser dimensional matrix to another device for reconstruction. The another device may in some examples be configured to utilize the lesser dimensional matrix to reconstruct the audio corresponding to the cough.

Examples described herein further include methods. An example method for reconstructing cough sounds may include receiving features extracted from an audio signal corresponding to cough sounds, wherein the features were extracted using basis vectors from a cough model and a lesser dimensional matrix based on a comparison between the basis vectors and the audio signal, reconstructing the features using the basis vectors and lesser dimensional matrix, and wherein the reconstructing results in reconstruction of the cough sounds but does not result in effective reconstruction of speech sounds in the audio signal.

In some examples, the basis vectors may be based on selected portions of a cough. In some examples, the cough model is not based on a final, wheeze phase of a cough.

In some examples, the features include features corresponding to cough sounds and further include features from the audio signal occurring within a specified period of time after the features corresponding to cough sounds.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings, in which:

DETAILED DESCRIPTION

Figure 1:
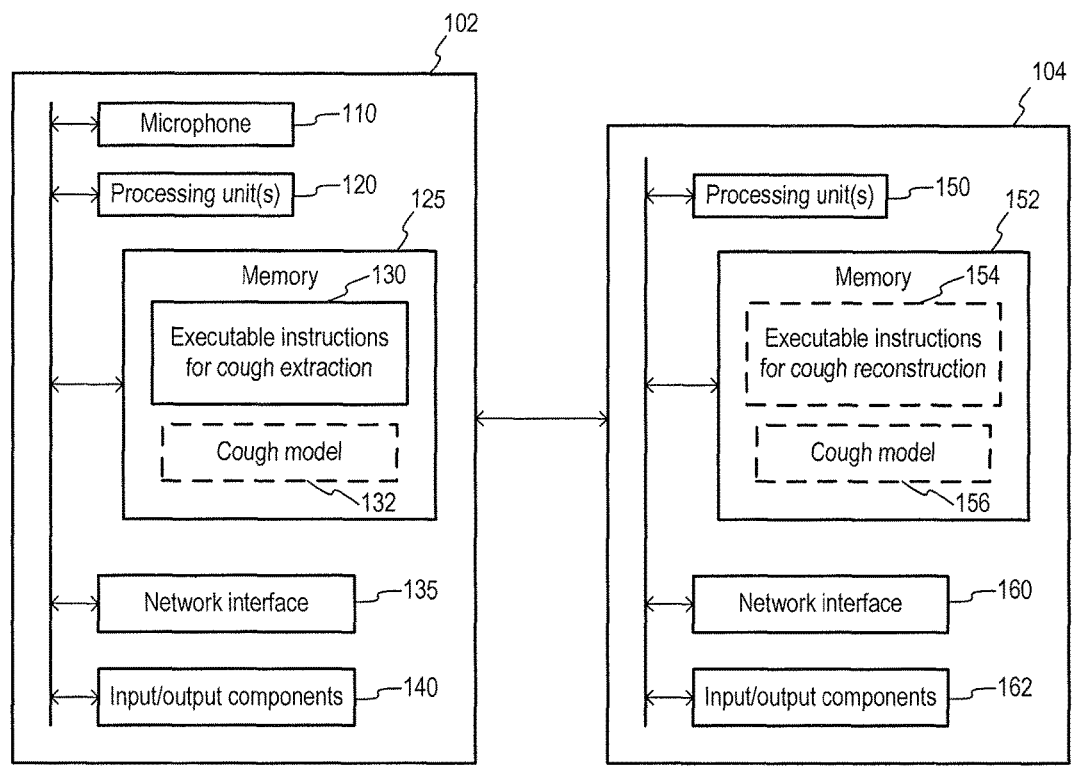
FIG. 1 is a schematic illustration of a system for detecting and reconstructing coughs in accordance with an embodiment of the present invention.

Certain details are set forth below to provide a sufficient understanding of embodiments of the invention. However, it will be clear to one skilled in the art that embodiments of the invention may be practiced without various specifics of these particular details. In some instances, well-known circuits, control signals, computer system components, timing protocols, and software operations have not been shown in detail in order to avoid unnecessarily obscuring the described embodiments of the invention.

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations.

An audio-based cough detection system is described which may effectively and inexpensively allow for the monitoring and automatic detection of coughs (e.g., without the need for self-reporting) while offering privacy preserving advantages. According to some examples, principal component analysis and classifiers, such as a random forest classifier, are used to detect desired audio features in an audio stream. Moreover, the audio signal corresponding to detected and stored audio features may be reconstructed with high fidelity from the isolated features while simultaneously preventing speech from being reconstructed with useful fidelity. In this manner, the audio privacy of the individual may be preserved. As will be appreciated the example systems and methods described may be implemented in a variety of platforms including mobile platforms, such as cell phones, which may facilitate ubiquitous yet non-invasive ambulatory monitoring of coughs.

According to an example method for detecting a cough, an audio signal may be received by a receiver, for example a microphone or other device that may convert sound pressure waves to an electronic signal. The received audio signal or portions thereof may be analyzed using a set of bases derived from principal component analysis (PCA) to provide a lesser dimensional representation of the analyzed audio signal or portion thereof. The lesser dimensional representation of the analyzed audio signal is created using basis vectors from a cough model. The lesser dimensional representation may be a projection from the cough model vectors on the spectrogram of all or a portion of the received audio signal and may serve as a comparison between the received audio and a cough sound. Accordingly, based on the comparison, the audio signal or portion thereof may be identified as a cough (or not). In some examples, when the audio signal or portion thereof is identified as a cough, the cough features may be extracted from the audio signal (e.g. the lesser dimensional representation of that portion of the audio signal and/or portions around it may be stored). If the portion of audio does not correspond to a cough, that portion may be discarded (e.g., not stored).

In some examples, the cough model may be based on only certain portions of a cough (e.g., initial portions of a cough) which are generally non-user specific. In this manner, one cough model may be used to identify coughs across multiple individuals.

Examples of the present invention further include reconstructing an audio signal corresponding to a cough from extracted features. Using the cough model, the extracted features may be reconstructed, and the cough replayed. In some examples, the cough model is provided such that it is sufficiently specific to enable reconstruction of cough sounds, but is ineffective for use in reconstructing other portions of the audio signal, such as speech. In this manner, a monitoring device, e.g., a cell phone may be used to record audio signals, features corresponding to coughs may be extracted, and reconstruction of only the cough sounds may take place by a healthcare provider or other recipient of the extracted feature information. Privacy of the monitored individual may be preserved because the cough model used to perform the reconstruction may be ineffective in reconstructing speech sounds that may also be included in the recording. In this manner, privacy of a user of the cough detecting device may be preserved from users later seeking to reconstruct the cough sounds, e.g., users of the computing system 104 of FIG. 1, which may be a healthcare provider (e.g., pulmonologist) or other monitor of the user of the cough detecting device 102.

While specifics of cough detection are described, it will be appreciated that the systems and methods described herein may be applicable to the detection of any of a variety of sounds, for example alarms, explosions, shattering of glass, or other sounds whose sound signature or spectrogram may be studied and a feature detection model developed according to the examples described herein.

FIG. 1 is a schematic illustration of a system for detecting and reconstructing coughs in accordance with an embodiment of the present invention. The system 100 includes a cough detection device 102 and another computing system 104. The cough detection device 102 may include a microphone 110 or similar receiver for receiving an audio signal. The cough detection device 102 may be configured to record the received sound or may provide the audio signals to other components in real-time as the signal is received by the microphone 110. Received sounds may be recorded, for example, in the memory 125 or other electronic storage accessible to the cough detection device 102. The memory 125 may be implemented using any non-transitory, physical, and/or tangible computer readable media. Non-transitory, physical, and/or tangible computer readable media include, but are not limited to, externally or internally attached hard disk drives, solid-state storage (such as, but not limited to, NAND flash or NOR flash media), tiered storage solutions, storage area networks, network attached storage, and/or optical storage. In examples where the audio signal is initially recorded locally on the device, the audio signal (or interchangeably referred to herein as audio stream) may be subsequently deleted following the cough detection analysis to aid in improving a user's privacy.

The cough detection device 102 may also include one or more processing unit(s) 120. The processing unit(s) may be implemented using one or more processors or other hardware capable of performing the analysis described herein. The memory 125 may further be encoded with executable instructions for cough extraction 130 that, when executed by the processing unit(s) 120 (e.g., by one or more processors), may cause the cough detecting device 102 to extract cough features from an audio signal as described herein. In further examples, the memory 125 or other memory or storage accessible to the cough detection device 102 may store executable instructions for cough classification, and/or executable instructions for cough reconstruction, which may cause the cough detecting device 102 further to classify coughs and/or reconstruct audio cough signals as described herein. The memory 125 further may store a cough model 132 which may be utilized to detect and/or to reconstruct cough sounds as described herein. The cough model 132 may be stored in the memory 125 and/or other memory or electronic storage accessible to the cough detecting device 102.

Examples of the cough model 132 are described herein. The cough model 132 may be stored in the cough detecting device 102 in some examples, may be downloaded from another location (not shown in FIG. 1), and/or may be accessed from another location in electronic communication or capable of electronic communication with the cough detecting device 102. In this manner, the cough model 132 may be updated either at the cough detecting device 102 or at the other location where it is stored.

The cough detecting device 102 may be implemented using any of a variety of computing systems such as, but not limited to, portable computing systems such as cellular telephones, personal digital assistants, tablet computers, or voice recorders. In some examples, a voice recorder may be used as the cough detecting device 102 and recorded audio signals and/or extracted features corresponding to coughs may be provided to another computing system, e.g., via transfer by a USB or other memory device. The cough detecting device 102 may include a network interface 135 for communication with other computing systems and/or storage resources. The cough detecting device 102 may further include any number of input and/or output components 140 such as, but not limited to, keyboards, keypads, touch screens and displays. In some examples, the cough detecting device 102 may be worn by a user, monitor audio, and extract features from the audio signal corresponding to cough sounds as described herein.

The executable instructions for cough extraction 130 and/or other executable instructions present in the cough detecting device 102 may be implemented by, for example, loading one or more applications onto the cough detecting device 125. The cough detecting device 125 may be programmed to perform cough detection, cough feature extraction, cough classification, and/or cough reconstruction using examples described herein.

In other examples, the microphone 110 may be present in a separate device (e.g., an audio recorder or other computing system) and may be used to record an audio stream. The recorded audio stream may be provided to the cough detecting device 102, e.g., received over a network, loaded from a memory or other storage media (e.g. USB drive, RAM, ROM) for extraction of cough features from the recorded audio stream.

The computing system 104 may be used to reconstruct sounds corresponding to a cough. While in some examples the cough detecting device 102 itself may include executable instructions for and function to reconstruct cough sounds, in other examples, the features extracted may be communicated, e.g. using the network interface 135, to the computing system 104. The communication may occur over any type of communication mechanism such as but not limited to the Internet, a cellular or other telephone network, or may occur by providing stored cough features to the computing system 104 (e.g. by providing storage containing the stored cough features in electronic communication with the computing system 104).

The computing system 104 may include one or more processing unit(s) 150 which may be implemented using one or more processors or other hardware capable of performing the analysis described herein. The computing system 104 may include a memory 152. The memory may be implemented using any non-transitory, physical, and/or tangible computer readable media. Non-transitory, physical, and/or tangible computer readable media include, but are not limited to, externally or internally attached hard disk drives, solid-state storage (such as, but not limited to, NAND flash or NOR flash media), tiered storage solutions, storage area networks, network attached storage, and/or optical storage. The memory 152 may be encoded with executable instructions for cough reconstruction 154. In other examples, the memory 152 may further include executable instructions for cough extraction and/or executable instructions for cough classification as described herein. However, in the example shown in FIG. 1, extracted features corresponding with a cough sound may be extracted by the cough detecting device 102 and provided to the computing system 104. The computing system 104 may reconstruct the cough sounds using the extracted features and a cough model, e.g., a cough model 156 which may also be stored in the memory 152 and/or may be stored in a different memory or other storage accessible to the computing device 104. The cough model 156 may be the same as cough model 132. In some examples, the cough model may be stored in a single or multiple locations accessible to both the cough detecting device 102 and the computing system 104.

The executable instructions for cough reconstruction 154 and/or other executable instructions present in the computing system 104 may be implemented by, for example, loading one or more applications onto the computing system 104. The computing system 104 may be programmed to perform cough detection, cough feature extraction, cough classification, and/or cough reconstruction using examples described herein.

As described herein, the cough model used to reconstruct coughs from extracted features may be sufficient to reconstruct the extracted cough features but may be insufficient to reconstruct other audio sounds, e.g., speech, that may also have been recorded by the microphone 110. Examples of cough models described herein include principal component analysis representations of a cough. The principal components may be used to extract features from an audio signal and then again to reconstruct the audio signal. However, because the cough model includes principal components indicative of a cough, the cough model may not be adequate for use in reconstructing other portions of the audio signal, such as speech.

The computing system 104 may further include a network interface 160 which may receive and/or provide data over a network from and/or to the cough detecting device 102. The network may be implemented as, for example, an internet, a cellular telephone network, or any other electronic communication mechanism. The computing system 104 may further include any number of input/output components such as, but not limited to, keyboards, displays, or touch screens.

While a particular example of an arrangement of components for the cough detecting device 102 and computing system 104 are shown in FIG. 1, it is to be understood that the arrangement of computing components according to examples of the invention is quite flexible. Any number of processors may be used, the described executable instructions may be distributed amongst several storage locations or consolidated into fewer, and responsibility for the various components of methods described herein may be given to different arrangements of devices. So long as the components described are in or able to be in electronic communication at the time when such communication is necessary, the components may form examples of the present invention regardless of which physical devices they reside in.

Figure 2:
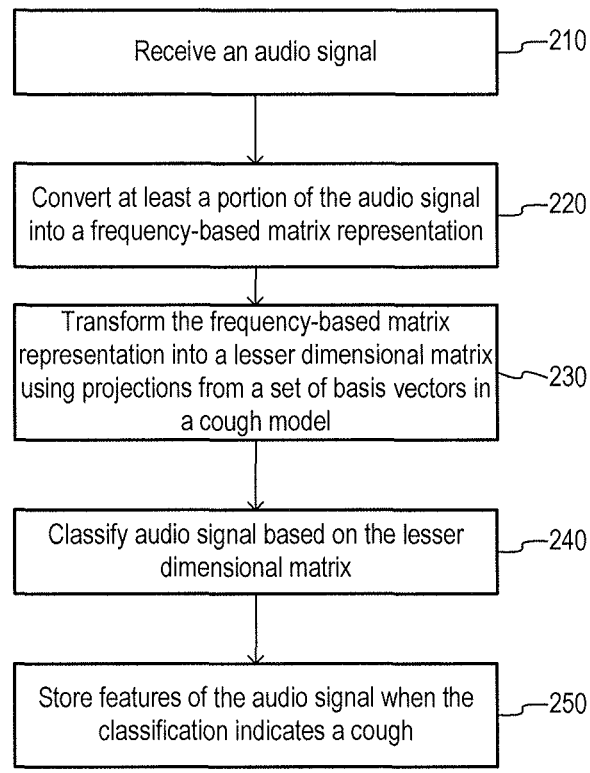
FIG. 2 is a flowchart of a method for cough detection according to an example of the present invention.

FIG. 2 is a flowchart of a method for cough detection according to an example of the present invention. An audio signal (e.g., audio stream) may be received as shown in box 210. The audio signal may be represented as an audio spectrogram. The spectrogram may generally be a data representation of the audio including a measure of how the spectral density of the audio signal varies with time. For example, the audio spectrogram may include amplitude of sound at particular frequencies over time. All or a portion of the audio signal may be converted into a frequency-based matrix representation in box 220. The conversion in box 220 may result in a representation of all or a portion of the audio signal that may include a matrix of sound amplitudes at particular frequencies.

Examples of the present invention may utilize a cough model to detect coughs in an audio signal. The cough model may be a data model including a plurality of eigenvectors of a spectrogram (e.g., the principal components of a portion of a cough spectrogram). Accordingly, the cough model may include a representation of audio spectrograms indicative of a known cough. The cough model may include any number of basis vectors (e.g., eigenvectors), 10 eigenvectors in one example, and any number of eigenvectors in other examples including 5, 6, 7, 8, 9, 11, 12, 13, 14, 15, 16, 17, 18, 19, 20, 21, 22, 23, 24, or 25 eigenvectors. The cough model may be generated by analysis of known cough sounds, such as by portions of audio spectrograms manually identified by listeners as cough sounds. The cough model may be represented as a matrix $X_N$ where N denotes the number of components in the model. Eigenvectors may be selected through this analysis which reliably describe cough sounds as distinguished from non-cough sounds. The eigenvectors may be eigenvectors of a covariance matrix of frequency-based matrix representations of audio signals corresponding to known cough sounds. Accordingly, multiple frequency-based matrix representations (e.g., spectrograms) of audio signals corresponding to known cough sounds may be provided, and a covariance matrix of those representations may be provided. Eigenvectors of that covariance matrix may be used as the basis vectors for a cough model. Moreover, in some examples, the cough model may be based on only portions of known cough sounds. In some examples, the fidelity of the reconstructed cough sound may be increased by using a larger number of components (for example larger than 10) at the expense of making speech more intelligible during reconstruction, which is a tradeoff to be evaluated as may be desired.

Some discussion of example physiology of cough sounds is provided herein by way of example and is not intended to be limiting as to the cough models or analysis techniques described herein. Irritation of afferent cough receptors in airways may trigger a cough reflex. Once triggered, the cough reflex may include four phases: (1) an initial deep inspiration and glottal closure, (2) contraction of the expiratory muscles against the closed glottis, (3) a sudden glottis opening with an explosive expiration, (4) a wheeze or "voiced" sound. The third and fourth phases of the cough reflex may generally be manifested as a cough sound. Cough sounds may share common attributes such as a relatively loud intensity, quick burst of sounds, and predictable duration and falloff. The overall energy of a cough reflex may be much stronger relative to the surrounding environment and the initial burst of air may cause significant energy, for example well into the 15 kHz range. During the fourth stage of the cough reflex, remaining air from the initial impulse may be pushed out of a vocal tract. It is this fourth stage of the cough which may cause coughs to sound different amongst different individuals as the pathological processes in the lungs may determine the characteristics of the sound based on how the lung tissue and vocal resonances are affected. Accordingly, this fourth stage of a cough may vary from person to person and may not be useful in cough detection across a larger population.

In some examples, accordingly, cough models used herein are based only on portions of coughs which are non-specific to users, e.g., the third or explosive stage of a cough. Stages of a cough which may be more likely to be user-specific (e.g. the fourth stage of a cough) may not be used to develop a cough model in examples of the present invention. Accordingly, cough models described herein, such as the cough models 132 or 156 of FIG. 1 or the cough model used in box 225 of FIG. 2 may be developed without using the fourth stage of known coughs (e.g., using only the explosive stage of known coughs). In one example, only the first 150 ms of cough sounds were used to develop cough models described herein. A complete cough sound may typically last 300 ms including the fourth, more personalized, cough stage. Other durations of cough sounds may be used to develop cough models according to examples of the present invention including the first 100 ms, 110 ms, 120 ms, 130 ms, 140 ms, 160 ms, 170 ms, and 180 ms.

Returning to the example method in FIG. 2, the audio signal (e.g., the frequency-based representation of the audio signal from box 220) may be compared with a cough model in box 230. The comparison may reduce the dimensionality of the frequency-based representation of the audio signal, resulting in a lesser dimensional matrix. The comparison may occur in accordance with principal component analysis, which generally uses orthogonal components (e.g., projections of eigenvectors) of a particular feature space to reduce dimensionality. The frequency-based representation provided by box 220 may be multiplied by a matrix vectors from a cough model, resulting in a representation of projections of the cough model vectors into the frequency-based representation of the audio signal, a generally lesser dimensional matrix. A selected number of projections may be selected for use in the lesser dimensional matrix, and remaining projections discarded (e.g., the projections may be sorted by eigenvalue and the largest eigenvalue projections retained). The lesser-dimensional matrix may in one example include 10 projections, although in other examples any number of projections may be used including 5, 6, 7, 8, 9, 11, 12, 13, 14, 15, 16, 17, 18, 19, 20, 21, 22, 23, 24, or 25 projections. The number of projections in the lesser-dimensional matrix of the audio signal may be selected to match a number of eigenvectors used in a cough model as described herein.

So, for example, the frequency-based representation of the audio signal or portion of audio signal may be compared with the cough model including principal components indicative of coughs. The lesser-dimensional matrix provided in box 230 may include a score for each of the principal components of the audio signal or portion thereof based on the vectors of the cough model. A plurality of scores (e.g. one score per eigenvalue) may be obtained in box 230 for use in determining whether or not the audio signal or portion thereof corresponds with a cough. The scores may represent entries in the lesser dimensional matrix which, as described above, may be generated by multiplying vectors from a cough model with the frequency-based matrix representation of the audio signal. The lesser dimensional matrix may also accordingly be referred to as a matrix of projection scores, where the lesser dimensional matrix includes scores representing a projection of the basis vectors of the cough model into the audio spectrogram.

Once a comparison has been performed with the cough model, one or more tiers of classification may be used to determine whether the audio signal or portion thereof corresponds with a cough sound in box 240. An initial or threshold analysis may be performed to filter out any features which fall below a predetermined threshold. For example, all of the scores obtained during the comparison in box 230 may be required to be at or above a threshold to indicate a cough sound. In other examples, a certain number of scores (e.g., corresponding to a certain number of eigenvalues) may be required to be above the threshold for the audio signal or portion thereof to be considered a cough sound. In some examples, higher fidelity classification techniques may be used. For example, tree classifiers, such as but not limited to a random forest classifier, may be used to classify a portion of the audio signal as a cough sound. The random forest classification may allow for increased accuracy and/or lower false positive as to which of the extracted features from the audio correspond to cough sounds. The thresholds and/or configuration information for the tree classifiers may be additionally included in cough models described herein, such as the cough model 132 and/or 156 of FIG. 1, or may be stored as separate cough models or cough model information.

Extracted features which are classified as a cough (e.g., determined to correspond to a cough sound) may be stored, as shown in box 250. The extracted features may correspond to a representation of the audio signal or portion thereof identified as corresponding to a cough sound. As described above, the cough model may be based on only certain portions, e.g., initial portions, of a cough sound. Accordingly, in some examples, the extracted features may correspond to the representation of the portion of audio signal corresponding to the cough sound as detected using the cough model plus an additional amount of the audio signal (e.g., 1, 2, 3, 4, or 5 additional seconds of audio signal). In some examples, additionally or instead, representations of portions of the audio signal preceding the detected cough may be stored (e.g., 1, 2, 3, 4, or 5 additional seconds of audio signal). The additional amount of audio signal may facilitate later reconstruction of the entire cough sound. The extracted features may be stored locally on the same device which receives the audio or they may be transmitted to a remote location (e.g., database). Other parameters, for example time of the cough, may also be recorded and used in further analysis, for example in determining duration, frequency, quality of cough, number of coughs, cough epochs, and the like. In this manner, the computing system 102 of FIG. 1 may further be configured (e.g., by being programmed with further executable instructions) to provide data (e.g., store data and provide the data to the computing device 104 or other remote device) regarding cough frequency, quality, length, number of coughs, cough epochs, and the like over time. Moreover, the computing system 104 may be configured to provide (e.g., display) data regarding the frequency, quality, length, number of coughs, and/or cough epochs (e.g., multiple coughs within a certain time combined to form one coughing episode). Such data may be useful for, e.g., pulmonologists in treating diseases characterized by coughing. Pulmonologists or other users of the computing system 104 of FIG. 1 may accordingly review a frequency, quality, length of time, number of cough epochs, etc. associated with the audio received by the device 102. As described further below, pulmonologists or other users of the computing system 104 may further replay the cough sounds.

Referring again to FIG. 2, the features stored in box 250 may correspond to the scores or other indication of the comparison from box 230. In some examples, only the scores or other features corresponding to portions of the audio signal where coughs were detected, or scores or other features corresponding to those portions plus some amount of data proximate to those locations, may be stored. In other examples, all scores or other features may be stored and indicators may also be stored of the portions corresponding to coughs. The extracted features may be the mean decibel energy of a Fast Fourier Transform (FFT) of all or a portion of the audio signal, the mean decibel energy of the FFT coefficients above 16 kHz (or other threshold in other examples), and below 16 kHz (or other threshold in some examples). The energy values, components weights, and residual error between a reconstructed cough sound and actual cough portion of the audio signal may be referred to as the extracted features.

The boxes 210, 220, 230, 240, and 250 of FIG. 2 may be performed, e.g., by the executable instructions for cough extraction 130 of FIG. 1 in cooperation with the processing unit(s) 120. Extracted cough features may further be stored in the memory 125 or other memory accessible to the cough detecting device 102. The executable instructions for cough extraction 130 of FIG. 1 may include instructions for performing any or all of the boxes 210, 220, 230, 240, and 250 of FIG. 2. In some examples, executable instructions encoded on the memory 152 of the computing system 104 of FIG. 1 may include instructions for performing any or all of the boxes 210, 220, 230, 240, and 250 of FIG. 2.

Figure 3:
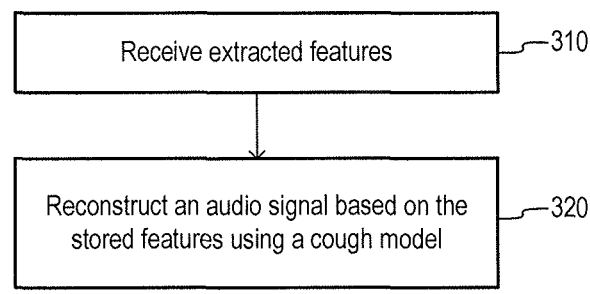
FIG. 3 is a flowchart of an example of cough reconstruction in accordance with an example of the present invention.

FIG. 3 is a flowchart of an example of cough reconstruction in accordance with an example of the present invention. In box 310, extracted features from an audio signal may be received. The extracted features may correspond to those, for example, stored in box 250 of FIG. 2. The extracted features may include the mean, normalization constant, and/or phase of the spectrogram in addition to projection scores, which may be used in reconstruction, examples of which are described further below. The extracted features may include the lesser dimensional matrices described above. These quantities may not increase privacy vulnerabilities of the system at least because phase and mean have typically been found to have little use in speech or speaker recognition.

The extracted features may be received, for example by the computing system 104 from the cough detecting device 102. In box 320, the audio signal may be reconstructed based on the stored features using a cough model. Recall a mean and projection scores (e.g., weights) may be received in box 310. In box 320, the spectrogram of the audio signal may be reconstructed using those projection scores, also referred to herein as a lesser dimensional matrix. In some examples, the reconstruction method performed in box 320 may include multiplying basis vectors of the cough model with the lesser dimensional matrix. The cough model used in reconstruction may be the same as the cough model used to extract the features. Reconstruction methods may in some examples be iterative and may be selected to minimize mean-squared error between a reconstructed frequency-based representation of the audio signal and the original frequency-based representation of the audio signal. The reconstruction may be expressed as: $a=\hat{X}_N \hat{X}_N^T(a-\bar{a})+\bar{a}$ where $\bar{a}$ is the mean of a and $\hat{X}_N^T(a-\bar{a})$ are the projection weights (an N element row vector). $X_N$, as described above, refers to the cough model. Stacking and normalization may be removed, and the phase of the original spectrogram (which may have been received as part of the features) may be reapplied. The extracted portions of the transformed audio (e.g., the extracted features) may be transformed again to the phase of the original spectrogram, and the spectrogram may be converted back to the time domain signal by: (1) performing the inverse short time Fourier transform (ISTFT) and (2) applying an inverse hamming window, as examples.

In this manner, portable devices such as cell phones and/or audio recorders may be used to continuously record sounds in the vicinity of a user. Sounds may include ambient noises, speech, coughs, sneezes, and other environmental noises occurring in the vicinity of the user. Events may be extracted from the audio recordings, either by the same device as performed by the recording or by a different device. The events may be extracted and then determined whether or not they correspond with cough sounds using PCA and a known cough model. The cough model may be stored on a device performing the analysis and/or may be downloaded from or accessed from another remote device. Features relating to cough sounds may be stored, and may be provided to the same or another device for reconstruction. Someone, e.g., a pulmonologist, interested in reconstructing the cough sound may conduct a reconstruction using the PCA cough model. The reconstruction may be effective to reconstruct cough sounds but due to the information provided as the extracted features and/or the cough model, other sounds such as speech sounds may be unable to be reconstructed.

Accordingly, systems and methods for detecting and enabling reconstruction of cough sounds have been described. The systems and methods may enhance user privacy by providing mechanisms for storing audio features corresponding to the coughs and cough models which are unable or ineffective to reconstruct speech sounds.

EXAMPLE

An example of a cough model generation process is described to aid in understanding and is not intended to be limiting.

In one example of generating a cough model which may be used in examples of the present invention, participants were provided with an Android G1 mobile phone and the phone was programmed with software to record sounds. A resulting 72 hours of audio were recorded from 17 participants. The audio recordings, made at a 32 kHz sampling rate, were manually annotated as cough, speech, laughter, breathing, throat clearing, sneezing, sniffing, other people's cough, and environmental noise.

The magnitude spectrogram of the entire audio sequence was taken (using a hamming window size of 16 ms, 50% overlap, and 512 point FFT). Annotated coughs were selected randomly for a training fold. For each cough, the first 150 ms of cough were placed in a single column vector and the vector normalized. Each column vector was concatenated to create a matrix of cough spectrograms, X. PCA was run on X, yielding a matrix of eigenvectors. The N components having the largest eigenvalues were saved, yielding a cough model $X_N$.

The training data spectrograms were reconstructed from $X_{10}$ and the projection weights used for reconstruction were saved along with the residual error of the reconstructed spectrogram. Three energy measures of the spectrogram were calculated, the mean decibel energy of the entire FFT, the mean decibel energy of the FFT coefficients above 16 kHz, and below 16 kHz. The energy values, component weights, and residual error were used as the feature set.

The feature set was used to generate an extraction methodology. The extraction methodology pruned the audio stream in search of events. A threshold was found at which 98% of the coughs in the training fold were retained regardless of false positives, and five features were selected that yielded a lowest false positive rate. The thresholds of those features were saved and used to prune the audio during evaluation.

A random forest classifier was trained on the feature set. The random forest classifier was set to weight cough errors more during the building of the forest and the majority voting threshold for the cough class was set to three times lower than non-cough sounds. The maximum number of trees was set to 500. The trained random forest classifier may be used in classifying cough sounds in further audio recordings.

For cough reconstruction, an optimal PCA reconstruction method was used, designed to minimize mean-squared error between the reconstruction and vector of interest. For a given spectrogram, 150 ms of adjacent columns were stacked into a normalized column vector, a. The reconstruction may be expressed as:

$a = \hat{X}_N \hat{X}_N^T (a - \bar{a}) + \bar{a}$ where $\bar{a}$ is the mean of a and $\hat{X}_N^T (a - \bar{a})$ are the projection weights (an N element row vector). This provided an estimate of the overall spectrogram magnitude for a 150 ms segment of audio. The stacking and normalization were removed, and the phase of the original spectrogram reapplied. The spectrogram was converted back into the time domain signal by (1) performing the inverse short time Fourier transform (ISTFT) and (2) applying an inverse hamming window.

The executable instructions for cough reconstruction 154 of FIG. 1 may include instructions for performing any or all of the boxes shown in FIG. 3. The executable instructions may be executed by the processing unit(s) 150 to perform the method shown in FIG. 3. In other examples, executable instructions for performing the method of FIG. 3 may be encoded in the memory 125 of the cough detecting device 102 and the cough detecting device 102 may be capable of reconstructing the cough sounds.

Although the present invention has been described with reference to specific examples, persons skilled in the art will recognize that changes may be made in form and detail without departing from the spirit and scope of the invention. Furthermore, while various aspects and examples have been disclosed herein, other aspects and examples will be apparent to those skilled in the art. The various aspects and examples disclosed herein are for purposes of illustration and are not intended to be limiting, with the true scope and spirit being indicated by the following claims.

What is claimed is:

1. A tangible computer readable medium encoded with instructions that, when executed, cause a computing system to;
    receive an audio signal from a microphone;
    convert at least a portion of the audio into a frequency-based matrix representation;
    transform the frequency-based matrix into a lesser dimensional matrix using projections from a set of basis vectors in a cough model to prevent reconstruction of speech sounds from the audio signal;
    classify at least a portion of the audio signal as corresponding, to a cough based, at least in part, on the lesser dimensional matrix;
    classify multiple portions of the audio signal as respective multiple coughs and the multiple coughs as a cough epoch, based at least in part, on the lesser dimensional matrix;
    reconstruct the at least a portion of the audio signal using multiplication of the basis vectors with the lesser dimensional matrix to provide a reconstructed audio signal, wherein the reconstructed audio signal excludes the speech sounds from the audio signal, wherein reconstruction includes implementation of an iterative reconstruction approach including minimizing differences between the frequency based representation of the at least a portion of the audio signal and a reconstructed frequency-based representation;
    provide data associated with the multiple portions of the audio signal, wherein the data includes a number of coughs and a number of cough epochs; and
    replay the reconstructed audio signal.

2. The computer readable medium of claim 1, wherein the frequency-based matrix representation of the at least a portion of the audio signal is an audio spectrogram.

3. The computer readable medium of claim 1, wherein the basis vectors of the cough model comprise eigenvectors of a covariance matrix of frequency-based matrix representations of audio signals corresponding to known cough sounds.

4. The computer readable medium of claim 1, wherein the basis vectors of the cough model comprise magnitude spectrograms of audio signals corresponding to known cough sounds.

5. The computer readable medium of claim 1, wherein the basis vectors of the cough model comprise complex spectrograms of audio signals corresponding to known cough sounds.

6. The computer readable medium of claim 1, wherein the instructions which, when executed, cause the computing system to classify at least a portion of the audio signal as corresponding to a cough include instructions for calculating a score for one or more of the basis vectors in the cough model.

7. The computer readable medium of claim 6, wherein the instructions that, when executed, cause the computing system to classify at least a portion of the audio signal as corresponding to a cough include instructions for comparing the calculated scores for the one or more basis vectors to threshold values and discarding portions of the transformed audio signal having calculated scores below a predetermined threshold value.

8. The computer readable medium of claim 1, wherein the instructions that, when executed, cause the computing system to classify at least a portion of the audio signal as corresponding to a cough include instructions for implementing a random forest classifier based on a comparison of the lesser dimensional matrix representation of the at least a portion of the audio signal with the basis vector representation of the cough model.

9. The computer readable medium of claim 1, wherein the cough model is a non-user specific cough model.

10. The computer readable medium of claim 1, wherein the computing system comprises a mobile phone.

11. The computer readable medium of claim 1, wherein the cough model is stored in a memory accessible to the computing system.

12. The computer readable medium of claim 1, wherein the instructions, when executed, further cause the computing system to store a duration of the cough, frequency of multiple coughs in the audio signal, number of coughs in the audio signal, cough epochs in the audio signal, or combinations thereof.

13. A device comprising:
    a microphone;
    at least one processor; and
    a memory encoded with computer readable instructions that, when executed, cause the at least one processor to:
        receive an audio signal from a microphone;
        convert at least a portion of the audio into a frequency-based matrix representation;
        transform the frequency-based matrix into a lesser dimensional matrix using projections from a set of basis vectors in a cough model to prevent reconstruction of speech sounds from the audio signal;

classify a portion of the audio signal as corresponding to a cough based, at least in part, on the lesser dimensional matrix;

classify multiple portions of the audio signal as respective multiple coughs and the multiple coughs as a cough epoch, based at least in part, on the lesser dimensional matrix;

reconstruct the at least a portion of the audio signal using multiplication of the basis vectors with the lesser dimensional matrix to provide a reconstructed audio signal, wherein the reconstructed audio signal excludes the speech sounds from the audio signal, wherein reconstruction includes implementation of an iterative reconstruction approach including minimizing differences between the frequency based representation of the at least a portion of the audio signal and a reconstructed frequency-based representation;

provide data associated with the multiple portions of the audio signal, wherein the data includes a number of coughs and a number of cough epochs; and replay the reconstructed audio signal.

14. The device of claim 13, wherein the device is a mobile phone.

15. The device of claim 13, wherein the memory is further configured to store the cough model.

16. The device of claim 13, wherein the device further comprises a network interface and wherein the instructions, when executed, further cause the at least one processor to transmit the lesser dimensional matrix to another device for reconstruction.

17. The device of claim 16, wherein the another device is configured to utilize the lesser dimensional matrix to reconstruct the audio corresponding to the cough.

18. A method for reconstructing cough sounds, the method comprising:

A microphone;

at least one processor;

a memory encoded with computer readable instructions that, when executed, cause the at least one processor to:

receive an audio signal from a microphone;

convert at least a portion of the audio into a frequency-based matrix representation; transform the frequency-based matrix into a lesser dimensional matrix using projections from a set of basis vectors in a cough model to prevent reconstruction of speech sounds from the audio signal;

classify a portion of the audio signal as corresponding to a cough based, at least in part, on the lesser dimensional matrix;

classify multiple portions of the audio signal as respective multiple coughs and the multiple coughs as a cough epoch, based at least in part, on the lesser dimensional matrix;

reconstruct the at least a portion of the audio signal using multiplication of the basis vectors with the lesser dimensional matrix to provide a reconstructed audio signal, wherein the reconstructed audio signal excludes the speech sounds from the audio signal, wherein reconstruction includes implementation of an iterative reconstruction approach including minimizing differences between the frequency based representation of the at least a portion of the audio signal and a reconstructed frequency-based representation;

provide data associated with the multiple portions of the audio signal, wherein the data includes a number of coughs and a number of cough epochs; and replay the reconstructed audio signal.

19. The method of claim 18, wherein the basis vectors are based on selected portions of a cough.

20. The computer readable medium of claim 1, wherein the data further includes cough frequency, cough length, and cough quality.

* * * * *